United States Patent [19]
Palathingal et al.

[11] Patent Number: 5,274,689
[45] Date of Patent: Dec. 28, 1993

[54] TUNABLE GAMMA RAY SOURCE

[75] Inventors: Jose C. Palathingal, Shirley; Kelvin G. Lynn, East Moriches; Palakkal Asoka-Kumar, Coram, all of N.Y.

[73] Assignees: University of Puerto Rico, San Juan, P.R.; Brookhaven National Laboratory, Upton, N.Y.

[21] Appl. No.: 988,752

[22] Filed: Dec. 10, 1992

[51] Int. Cl.⁵ .............................................. H01J 35/00
[52] U.S. Cl. ..................................... 378/119; 378/210
[58] Field of Search ........................................ 378/119

[56] References Cited

U.S. PATENT DOCUMENTS

| | | | |
|---|---|---|---|
| 3,234,099 | 2/1966 | Baldwin et al. | 176/16 |
| 3,924,125 | 12/1975 | Murray | 250/303 |
| 3,999,096 | 12/1976 | Funk et al. | 313/330 |
| 4,125,773 | 11/1978 | Aldenhovel | 250/413 |
| 4,341,731 | 7/1982 | Mills, Jr. | 376/156 |
| 4,463,263 | 7/1984 | Padawer | 250/363 |
| 4,845,371 | 7/1989 | Stieber | 250/505.1 |
| 4,845,732 | 7/1989 | Michel | 378/119 |
| 4,962,317 | 10/1990 | Jason et al. | 250/396 |
| 5,019,712 | 5/1991 | Knauer | 250/423 R |

FOREIGN PATENT DOCUMENTS 276437 8/1988 European Pat. Off. .

OTHER PUBLICATIONS

Thorn et al.; The LEGS electron spectrometer for tagging backscattered photons Nuclear Instruments and Methods in Physics Research A285:447-458 (1989).

Lindenstruth et al.; Measurements and simulations of low enery, thick target bremsstrahlung spectra; Nuc. Instr. Meth. Physics Res. A300:293-296 (1991).

Palathingal et al.; Single-quantum annihilation of positrons with shell-bound atomic electrons; Physical Rev. Letters 67:3491-3494 (1991).

Primary Examiner—Craig E. Church
Attorney, Agent, or Firm—Olive & Olive

[57] ABSTRACT

A source of gamma rays (a photon beam) at a single energy produced by the single-quantum annihilation of accelerated positrons with electrons of a target element. The photons are emitted predominantly in the forward direction and are accompanied by background radiation which can be differentially suppressed. The energy of the photons is determined by varying the energy of incident positrons. The photon beam is usable in materials research and analysis, medical diagnosis and therapy, and numerous other fields.

22 Claims, 4 Drawing Sheets

TUNABLE GAMMA RAY SOURCE

STATEMENT AS TO RIGHTS IN INVENTION

This invention was made with Government support and the Government has certain rights in the invention.

BACKGROUND OF THE INVENTION

1. Field of the Invention

This invention relates to nuclear radiation, and in particular, relates to the production of a photon beam having a single high energy which is tunable.

2. Description of the Related Art

Gamma rays are high energy photons, generally emitted from radioactive nuclei. Various studies have been done in an attempt to produce a tunable monoenergetic photon beam. For example, Lindenstruth et al., Nuclear Instruments and Methods in Physics Research, Vol. A300:293 (1991), performed nuclear resonance fluorescence experiments on selected radioactive isotopes to determine the relative spectral shape of low energy thick target bremsstrahlung spectra. The disclosure of this paper and of all other papers and patents cited herein is incorporated herein by reference. The emission of bremsstrahlung by charged particles in flight is limited in that this radiation has the characteristic of a continuous electromagnetic spectrum, and the photon energy ranges from zero to a finite limit. To obtain a monoenergetic beam using bremsstrahlung spectra, radiation of a particular bandwidth would need to be tagged and sorted out, requiring complicated electronic procedures and resulting in a low gamma ray yield per particle of the incident beam. This process is cumbersome and results in many "noise" photons at undesired energies, and large bandwidth of the selected photon beam.

Other researchers have attempted to utilize Compton scattering of laser photons from an incoming beam of highly-relativistic particles to develop a tunable gamma ray source. Thus, Thorn et al., Nuclear Instruments and Methods in Physics Research A285:447 (1989), described a spectrometer for tagging a gamma ray beam produced by Compton backscattering laser light from an electron beam circulating in a storage ring.

Satisfactory tunable monoenergetic beams of photons have therefore not been produced, and there has been no known way to obtain such a monoenergetic beam with a variable energy. Such beams have many potential uses, for example, in medicine to determine the presence of a particular element in the body without over-exposing the body to a multitude of extraneous wavelengths of radiation.

Single quantum annihilation of positrons is recognized as a fundamental electrodynamic process of atomic physics, but not many studies have been made of this phenomenon. Thus, when a positron, which does not decay spontaneously, passes through matter it sooner or later collides with an ordinary electron. In this collision, the positron is annihilated, and the total energy of the positron and the electron is converted into electromagnetic radiation in the form of one or more photons.

Single quantum annihilation of a positron in flight with a bound atomic electron takes place in the Coulomb field of the nucleus. The K-shell of the atom is responsible for about 80% of the annihilation, with electrons in the higher shells contributing the rest of the annihilation. The energy of the photon is given by $E_\gamma$. $= E + 2Mc^2 - B$, with $mc^2$ representing the rest-mass energy of the electron/positron, and B the binding energy of the atomic electron that is annihilated with the positron.

For any particular atomic shell, it is postulated that the photons obtained by annihilation are highly monoenergetic, the energy width being accounted predominantly by the energy divergence of the incident positrons and the spread introduced as the positrons traverse the target material. The net energy width of the emitted photons, in terms of the incident-energy divergence $\delta E$ of the positrons and the thickness $\mu$ of the target, is given as:

$$\delta k = \{\delta E^2 + (\mu dE/d\mu)^2\}^{\frac{1}{2}},$$

where $dE/D\mu$ represents the energy depletion rate of the positrons for transmission in the target material, which is typically around 1 keV//(mg/cm$^2$). Previous work, however, has not yielded a method or apparatus for producing monoenergetic photons, the energy of which is tunable (adjustable in energy).

It is therefore an object of this invention to provide an apparatus and method for producing a tunable source of monoenergetic photons.

It is a further object of this invention to provide means of producing a beam of protons which is highly directional and forward peaked (is self-collimated), and is polarizable.

It is a further object of this invention to provide a means of producing a beam of photons which can have a very narrow width, which can be regulated by regulating the width of an incident beam of positrons and the thickness of the target.

It is a further object of this invention to provide a means of producing a beam of photons with an intensity which is high in proportion to the intensity of the incident positrons as compared to previous methods of obtaining monoenergetic photons of variable energy.

It is another object of this invention to provide a source of monoenergetic photons which does into depend on the use of a tagging device.

Other objects and advantages will be more fully apparent from the following disclosure and appended claims.

SUMMARY OF THE INVENTION

The invention includes an apparatus for providing a collimated photon beam (also termed gamma rays) having a single but variable energy, comprising:
(a) a source of positrons which is adjustable to the extent of being able to provide a collimated beam of positrons of a selected precise single energy; and
(b) a target located in the path of said beam and operative by single quantum annihilation of incoming positrons to produce and outgoing substantially unidirectional beam of photons of a single energy related to the selected energy of the beam of positrons.

Preferably, said source of positrons includes means enabling the energy of the positron beam to be varied to thereby cause a corresponding change in the energy of the photon beam enabling said photon beam to be tuned.

The method of the invention of providing a monoenergetic beam of photons, comprises providing a monoenergetic beam of accelerated positrons having a forward direction, said beam of positrons incident on a thin target located in the path of said beam of positrons, so that a monoenergetic beam of photons is produced by single quantum annihilation of said positrons and is emitted from said target predominantly in said forward direction.

The beam of photons produced by the invention is highly unidirectional, of a fine bandwidth and is polarizable. The photons are produced by the single-quantum annihilation of accelerated positrons with electrons in a target element, preferably a heavy element, for example uranium or lead. Preferably a uranium target is used. The positrons may be obtained from a strong positron source coupled, for example, with a spectrometric separation facility, a particle accelerator, a storage ring, in a pulsed mode or continuous-beam mode, or any other known means for producing a monoenergetic beam of positrons. A "strong" source includes, for example, any positron source which allows production of an intense photon beam. Experimental evidence indicates that a beam of $10^{10}$ positrons/second provides a sufficiently intense photon beam for the purposes discussed herein. The energy of the photons may be varied over a large range by varying the energy of incident positrons. The gamma radiation has a spectral distribution around a dominant peak dominated by a single line directly and linearly related to the energy of the incident positrons, with the rest of the spectrum consisting of a few weaker lines and a lower energy continuous background radiation of generally lower differential intensity (intensity per unit interval of photon energy). The photon beam is usable in materials research and analysis, medical diagnosis and therapy, and numerous other fields.

The invention may be varied in many ways, for example, by using positrons of different energy ranges, using targets of different material or thickness, by polarizing the positrons prior to reaching the target so that they may be used in particular applications in science and technology, differential absorption of background radiation associated with the photon beam, deflection of non-annihilated positrons emerging from the target, tagging for background suppression, for example, of bremsstrahlung and two-quanta radiation, and by single-quantum annihilation photon tagging.

Other aspects and features of the invention will be more fully apparent from the following disclosure and appended claims.

DETAILED DESCRIPTION OF THE INVENTION PREFERRED EMBODIMENTS THEREOF

Figure 1:
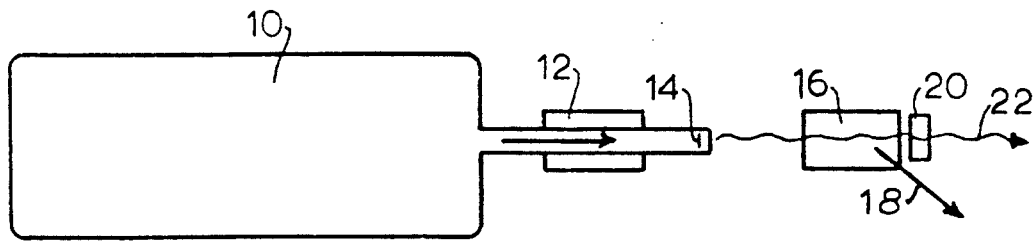
FIG. 1 is a diagrammatic representation of the invention in which a particle accelerator is used to produce the positrons.

The present invention provides a source of monoenergetic photons. Under appropriate conditions, single-quantum annihilation of a monoenergetic beam of positrons in a thin target yields a spectrum of gamma rays dominated by a single spectral line. The photon energy of this spectral line is directly and linearly related to the energy of the incident positrons, and therefore can be varied arbitrarily and easily by varying the energy of the positrons. The gamma ray beam produced by single-quantum annihilation has an exceptionally high energy resolution (fine bandwidth) which can be as small as around 1 keV at MeV energies. The photons are emitted predominantly in the forward direction, meaning the same direction in which the positrons are aimed. Non-annihilated positrons emerging from the target are preferably deflected off laterally by a transverse magnetic field. An intercept is preferably used to differentially suppress (absorb) the "soft component" of the continuous gamma ray spectrum accompanying the single-quantum annihilation radiation. Photons emerging from the intercept, dominated by the single-quantum annihilation photons, may be polarized as desired by having the positrons pass through a longitudinal magnetic field upstream of the target.

The photon yield of the invention is high compared with other non-single quantum annihilation systems. Thus, the photon yield of the single quantum annihilation device, using 10 MeV energy and a 1 mg/cm$^2$ uranium target may be $10^{-6}$/sr·keV per positron, which is orders of magnitude higher than the yields reported to be possible with sources based on bremsstrahlung and laser scattering. With a positron facility yielding currents in the $\mu$A or mA range, very large monoenergetic photon fluxes become available.

The beam of positrons may be derived from radioactive sources coupled with spectral devices or from accelerators, at any energy above zero. In the preferred embodiment an accelerator, such as the Brookhaven National Laboratory (Upton, New York) Dynamitron is used which can provide positrons in the energy range of 0.5 to 3.0 MeV. The current state of the technology allows production of positrons at up to hundreds of MeV in high-intensity beams, and thus the resultant photon beams might have energies variable, for example, from 1 MeV to hundreds of MeV using technology now known.

The preferred target used in the invention is a heavy element such as uranium. The reason for this is that the cross section ($\sigma_s$) for the single-quantum annihilation (SQA) process increases with the atomic number Z of the target as $Z^5$, whereas the cross-section ($\sigma_t$) for two-quantum annihilation (TQA) and bremsstrahlung ($\sigma_b$) are not as dependent on the atomic number Z. The single-quantum annihilation events are accompanied by two major physical processes that also occur in the target: two quantum annihilation of the positrons in flight, and bremsstrahlung. The relative photon yields are determined by their cross-sections. Cross-section relations for single-quantum annihilation have been determined to be of the order in Table 1, which shows a lower cross-section for single-quantum annihilation, but the photon energies of the two-quantum annihilation and the bremsstrahlung are spread over larger ranges of energy as shown in Table 2.

TABLE 1

| E MeV | Integral Cross-sections (barns/atom) | | |
|---|---|---|---|
| | $\sigma_s$ | $\sigma_t$ | $\sigma_b$ |
| 1.0 | 1.10 | 5.39 | 15.1 |
| 10 | 0.104 | 0.393 | 44.3 |
| 100 | 0.010 | 0.061 | 58.6 |

TABLE 2

| E MeV | Spectral Ranges: Photon Energy (MeV) | | |
|---|---|---|---|
| | SQA line width | TQA | Bremsstr. |
| 1.0 | 0.0014 | 0.86 | 0.49 |
| 10 | 0.0014 | 9.98 | 9.49 |
| 100 | 0.0014 | 100 | 99.5 |

The differential cross-sections for the three processes clearly favor the use of single-quantum annihilation (Table 3).

TABLE 3

| E MeV | Average Differential Cross-sections, $d\sigma/dk$ (millibarns/keV) | | |
|---|---|---|---|
| | SQA K line | TQA | Bremsstr. |
| 1.0 | 630 | 6.3 | 31 |
| 10 | 59 | 0.039 | 4.7 |
| 100 | 5.7 | 0.0006 | 0.59 |

The preferred thickness of the target is related to the desired width (bandwidth) of the single-quantum spectral and the need that the process provide an adequate photon yield. For the ideal source of monoenergetic photons, the bandwidth should be the narrowest possible. In such a case, a target thickness of about 1 mg/cm$^2$ is suitable.

Preferably an absorber as is known in the art is used for differential attenuation of the low-energy region of the gamma radiation, which is derived from two-quantum annihilation and bremsstrahlung. For positrons incident at low energies, the photons are of proportionately low energy, and a high Z element such as lead serves as a good differential absorber. When the photon energies are approximately several MeV's or over, an intercept of a light element alone is effective. Thus, hydrogen can be used in this case to attenuate the low energy region. The absorber should be thick enough to provide the desired attenuation but not compromise the intensity of the singlequantum annihilation.

FIG. 1 is a diagrammatic representation of the invention adapted to utilize the positron beam from a particle accelerator 10 for producing a polarizable, continuous-beam, tunable gamma ray source. The accelerated positron beam passes through the magnetic field produced by a current-carrying solenoid 12 before being incident on the target 14. A magnetic field having a line integral 200 Gauss.meter can polarize the positrons by nearly 100%, and can be easily produced, for example, by a cylindrical winding of copper wire carrying a DC electric current. The positrons emerging from the target which are not annihilated are deflected off by a transverse magnetic field 16 in a lateral direction 18. The photons exiting from the differential absorber 20 make up the tunable gamma ray (photon) beam 22.

Figure 2:
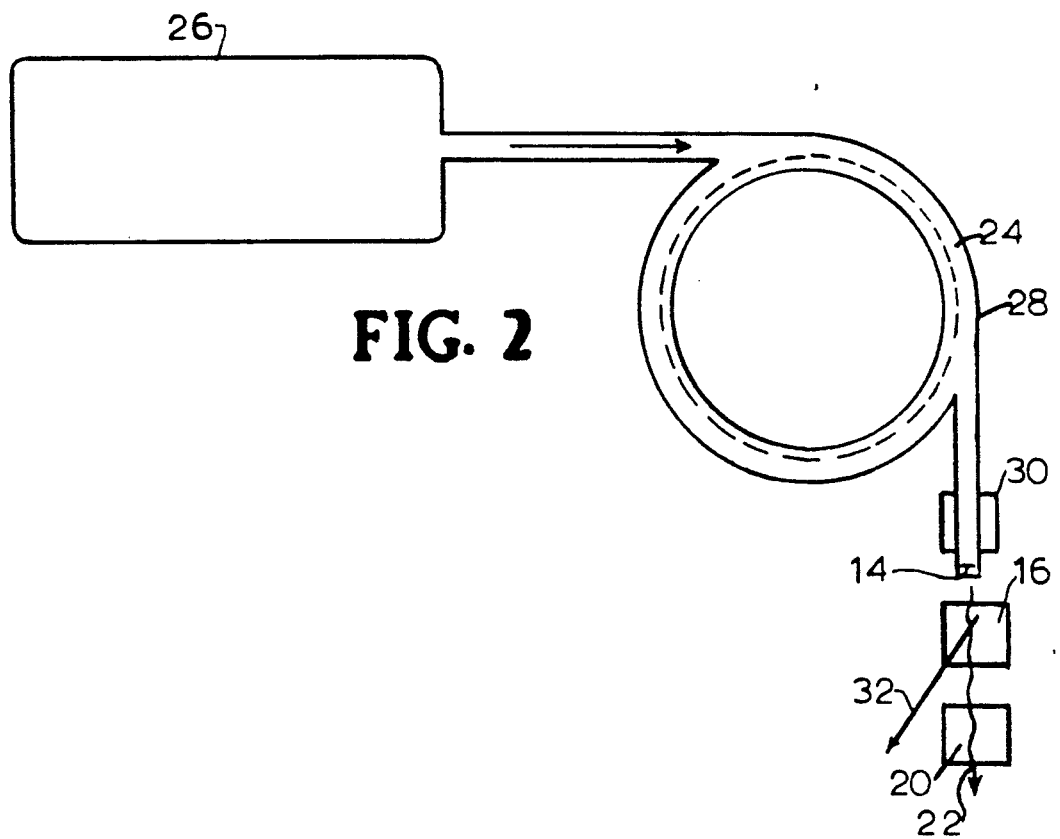
FIG. 2 is a diagrammatic representation of the invention in which a positron-storage ring is used to produce the positrons.

FIG. 2 is a diagrammatic representation showing a positron storage ring 24 which may be used to yield high-energy positrons of a single energy in a pulsed mode or a continuous beam mode at very high fluxes, and thus may result in a pulsed or continuous beam, tunable gamma ray source of high energy photons. Pre-accelerated positrons from an injector 26 enter the storage ring 24. The beam of positrons is drawn out by an appropriate extractor 28, is passed through a polarizing longitudinal magnetic field 30, and then strikes the target 14. Alternatively, the target may be placed in the storage ring out of the storage beam line, as shown by the dotted lines, with the path of the positrons being deviated to have them pass through the target. The non-annihilated positrons 32 are deflected off by a transverse magnetic field 16, and the photon beam 22 emerges through the differential absorber 20 of liquid hydrogen.

Figure 3:
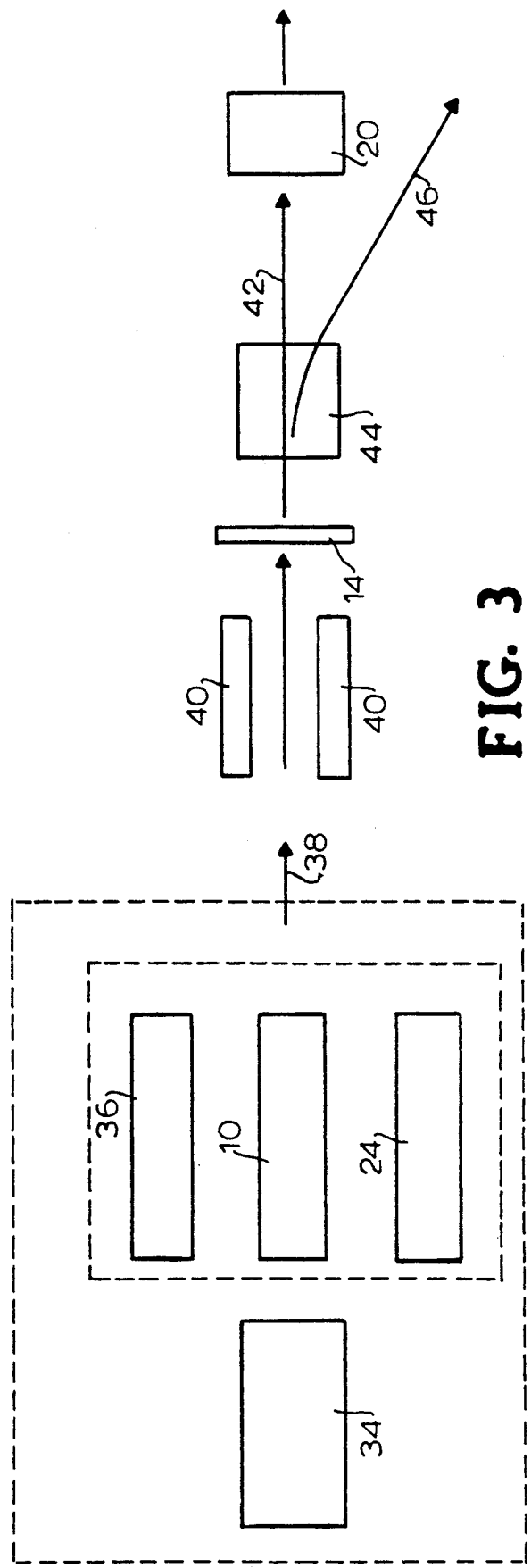
FIG. 3 is a diagrammatic representation of the invention showing a number of the various optional features.

FIG. 3 is an overall schematic diagram of the various preferred components of the invention. The positrons from a strong positron source 34 enter any means for creating a monoenergetic beam of accelerated positrons of regulated width and energy. Shown are a spectrometric separation facility 36, which may be, example, a beta-ray spectrometer; a positron accelerator 10; and a positron storage ring 24. The exiting monoenergetic beam 38 of positrons of a regulated width may optionally be passed through a polarizing means 40 prior to reaching the target 14. The resultant monoenergetic beam 42 of photons exiting the target 14 may then optionally be passed through a differential absorber 20 of background radiation before being used for their chosen purpose. Non-annihilated positrons emerging from the target may be deflected by deflector means 44 as known in the art so that they are not part of the photon beam 42.

The components of the apparatus of the invention, which are used in the method of the invention, are those known in the art of radiation science. The photons produced by the invention may be used in many ways as are known by those of skill in the art of radiation science, for example, in a device for material analysis, for measurement of masses, dimensions, shapes, densities and material composition of bodies and structures, in geological, geophysical, geographical, environmental, underwater, oceanographic, meteorological, chemical or biological analysis and studies, in a device for exploration of space or spacial objects, in a trigger device, in a signalling or communication device, in a pulsing device, in a plasma production device, in a device for medical diagnosis or therapy, and in a radiation generating device.

The features and advantages of the present invention will be more clearly understood by reference to the following examples, which are not to be construed as limiting the invention.

EXAMPLES

Example 1

Figure 4:
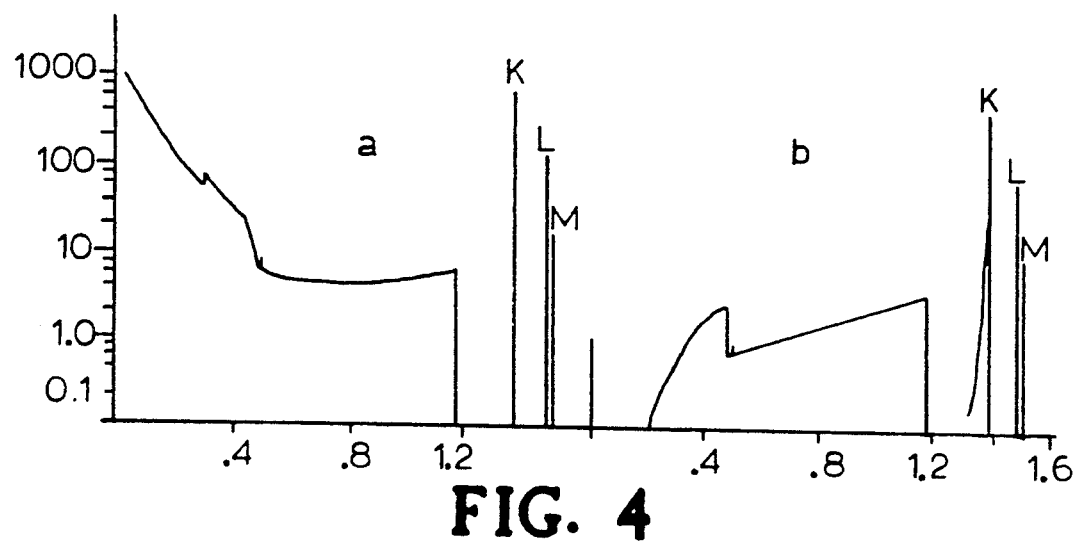
FIG. 4(a) is a graph of the total radiated spectrum at a positron energy of 1 MeV.
FIG. 4(b) is the spectrum transmitted through the differential absorber of specified material and thickness.
Figure 5:
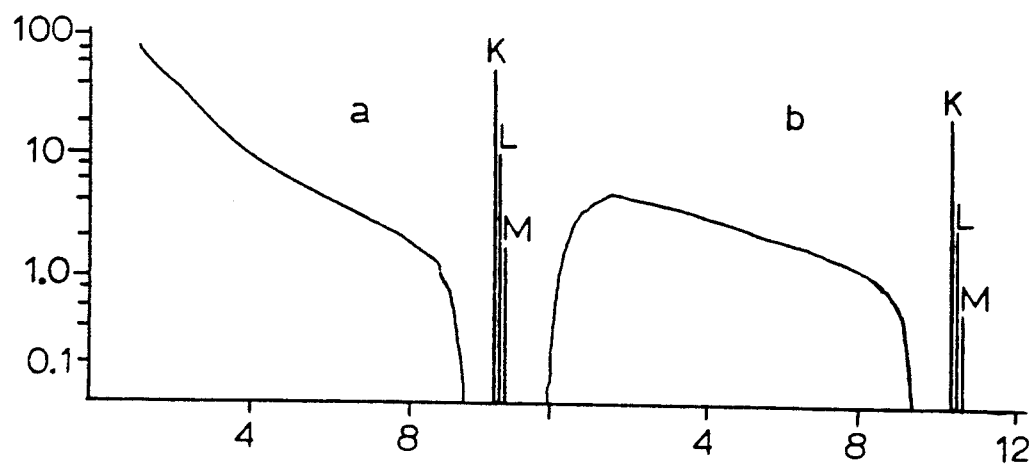
FIG. 5(a) is a graph of the total radiated spectrum at a positron energy of 10 MeV.
FIG. 5(b) is the spectrum transmitted through the differential absorber of specified material and thickness.
Figure 6:
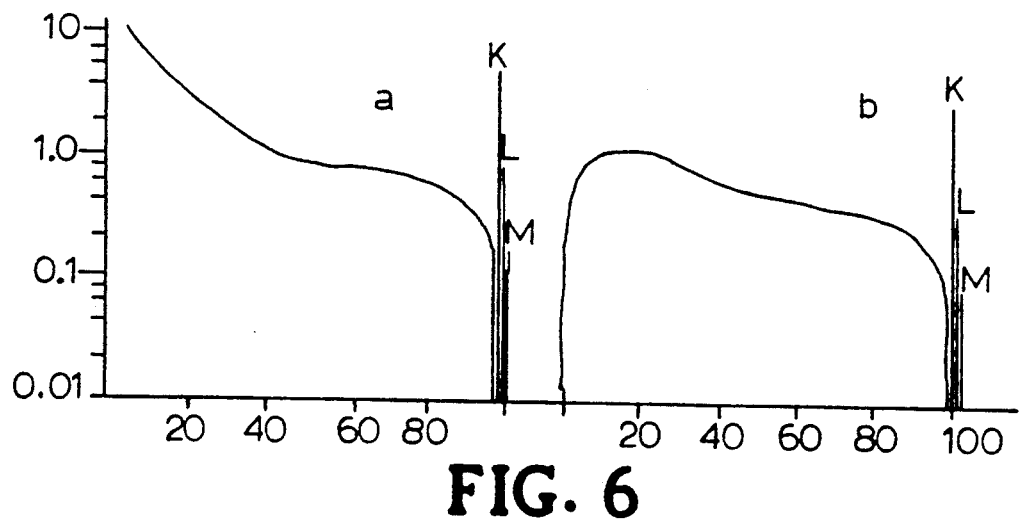
FIG. 6(a) is a graph of the total radiated spectrum at a positron energy of 100 MeV.
FIG. 6(b) is the spectrum transmitted through the differential absorber of specified material and thickness.

FIGS. 4, 5 and 6, respectively, show the radiation spectra of gamma radiation obtained at 1, 10 and 100 MeV using a uranium target of 1 mg/cm$^2$. Part (a) of each Figure shows the total radiated spectrum at a particular positron energy, and part (b) of each Figure shows the spectrum transmitted through the differential absorber of specified material and thickness. The thickness chosen in each case is the equivalent of one halfabsorption thickness for the K-shell/single-quantum annihilation line. Thus, FIG. 4, shows use of a positron energy of 1 MeV and a 12.3 g/cm$^2$-thick lead plate. For the higher energy cases shown in FIGS. 5 and 6 (10 and 100 MeV), liquid-hydrogen columns, 21.8 g/cm$^2$ and 58.7 g/cm$^2$, respectively, are used as the absorber. The K-single-quantum annihilation line intensity is reduced by 50% of that produced in the target due differential absorber, but the lower energy region of the continuous background is suppressed to a much greater extent than is the desired energy region. In each of these figures, the single-quantum annihilation lines are assumed to have a width of 1.4 keV, which is a very fine bandwidth only possible with single-quantum annihilation. As shown in these Figures, the optimum positron energy for production of monoenergetic photons is below about 10 MeV; above this value the quality of the tunable device of the invention decreases.

Example 2

Experiments were conducted using the Brookhaven Dynamitron at approximately 1.0, 1.5, and 2.0 MeV. Results confirmed the spectral shape represented in FIG. 4(a) that led to the concept of feasibility of a tunable gamma ray source. Other results are shown in Palathingal et al., Physical Review Letters 67:3491 (1991), the disclosure of which is incorporated herein.

Example 3

This example describes an instrument for nondestructive material analysis, based on a tunable gamma ray source. The whole body content of individual elements contained in a sample of material (for example, a piece of rock) can be determined nondestructively, element by element, with a tunable gamma ray source. The photon energy is tuned to different values, each value being appropriate for searching a particular element. Examples of the photon energies and the elements that can be looked for in the rock sample at these energies are, for example:

| Element | Photon Energy |
|---|---|
| Sodium | 2.982 MeV |
| Magnesium | 4.238 MeV |
| Aluminum | 2.981 MeV |
| Potassium | 2.523 MeV |
| Chromium | 3.162 MeV |
| Iron | 3.370 MeV |
| Nickel | 3.264 MeV |
| Copper | 2.336 MeV |

Figure 7:
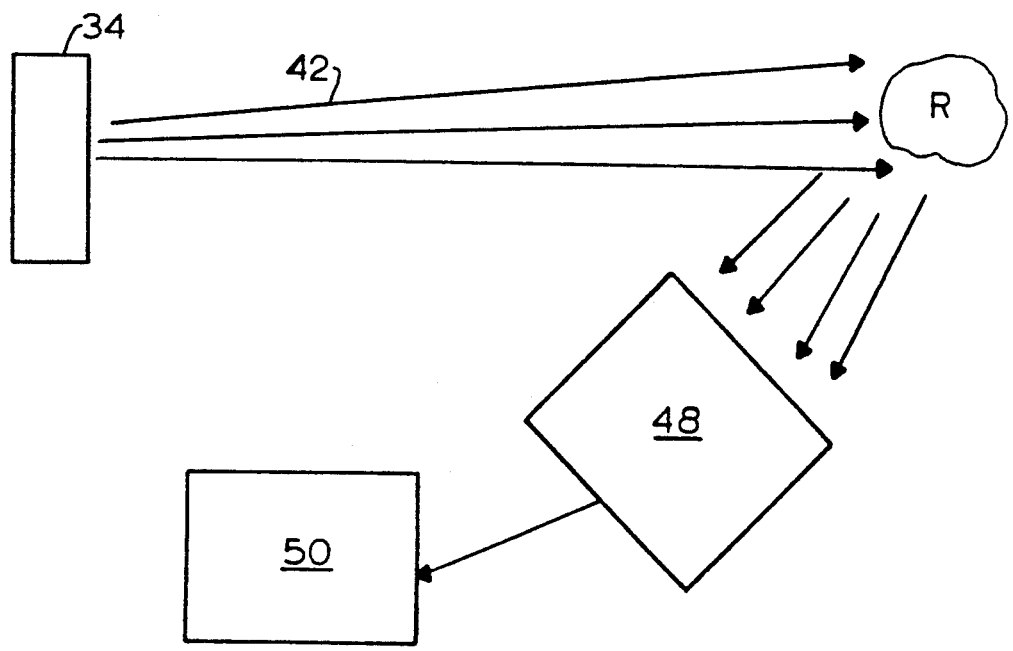
FIG. 7 is a schematic diagram of the apparatus described in Example 3.

The operating principle behind the technique is the nuclear resonance fluorescence of the gamma rays produced by the tunable gamma ray source of the invention. The apparatus, shown schematically in FIG. 7, consists of the following:

1) A tunable gamma ray source 34 with 10$^6$ photons/second, and energy spread of 1 keV.

2) A rock sample R roughly of size 3 cm in any direction

3) Photon detector 48 for scattered photons from the rock R: HPGe Detector of 100% relative efficiency, Model GEM-100220 (EG & G Ortec, Oak Ridge, TN)

4) Multichannel Analyzer 50 (computerized) of signals from the detector 48, Model PCA-II (Tennelec/-Nucleus Inc., Oak Ridge, TN)

A 15-minute exposure of the rock sample provides, for example, an estimated content of copper in the rock sample body with a sensitivity of about one percent. A one-hour exposure can yield a sensitivity of ½ percent.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What Is Claimed Is:

1. An apparatus providing a collimated photon beam having a single but variable energy, comprising:
    (a) a source of positrons which is adjustable to the extent of being able to provide a collimated beam of positrons of a selected precise single energy; and
    (b) a target located in the path of said beam and operative by single quantum annihilation of incoming positrons to produce an outgoing substantially unidirectional beam of photons of a single energy related to the selected energy of the beam of positrons.

2. An apparatus according to claim 1, wherein said source of positrons includes means enabling the energy of the positron beam to be varied to thereby cause a corresponding change in the energy of the photon beam enabling said photon beam to be tuned.

3. An apparatus according to claim 1, wherein said source comprises:
    (a) a strong positron source; and
    (b) means for converting radiation from said strong positron source to said single energy beam of positrons of selected width, said means selected from the group consisting of a spectrometric separation facility, a positron accelerator and a positron storage ring.

4. An apparatus according to claim 1 wherein said target comprises uranium.

5. An apparatus according to claim 1, further including means to polarize said beam of positrons prior to reaching said target.

6. An apparatus according to claim 1, wherein said beam of photons is dominated by a single line directly and linearly related to the energy of the incident positrons.

7. An apparatus according to claim 1, further including means located downstream from said target and operative to deflect non-annihilated positrons emerging from the target.

8. An apparatus according to claim 1, wherein said target comprises a heavy element.

9. An apparatus according to claim 1, further including means to absorb background radiation associated with said photon beam.

10. An apparatus according to claim 1, wherein the energy width of the positrons and the thickness of the target regulate to the bandwidth of the photon beam.

11. An apparatus according to claim 1, wherein said source is operable in a pulsed mode.

12. An apparatus according to claim 1, wherein said source is operable in a continuous-beam mode.

13. An apparatus according to claim 1, wherein said photon beam has a substantially fine bandwidth.

14. A method of providing a tunable monoenergetic beam of photons, comprising providing a monoenergetic beam of accelerated positrons having a forward direction, said beam of positrons having an energy which is controllable and being incident on a thin target located in the path of said beam of positrons, so that a monoenergetic beam of photons is produced by single quantum annihilation of said positrons and is emitted from said target predominantly in said forward direction.

15. A method according to claim 14 wherein said beam of positrons is obtained from a source selected from the group consisting of a spectrometric separation facility, a positron accelerator and a positron storage ring.

16. A method according to claim 14 wherein said target comprises uranium.

17. A method according to claim 14 wherein positrons are obtained from a source including means enabling the energy of the positron beam to be varied to cause a corresponding change in the energy of the photon beam enabling the photon beam to be tuned.

18. A method according to claim 14, further including providing means to polarize said beam of positrons prior to reaching said target.

19. A method according to claim 14, further including providing means located downstream from said target and operative to deflect non-annihilated positrons emerging from the target.

20. A method according to claim 14, further including providing means to absorb background radiation associated with said photon beam.

21. A method according to claim 14, wherein said monoenergetic positrons are obtained in a pulsed mode.

22. A method according to claim 14, wherein said monoenergetic positrons are obtained in a continuous-beam mode.

* * * * *

UNITED STATES PATENT AND TRADEMARK OFFICE
CERTIFICATE OF CORRECTION

PATENT NO. : 5,274,689

DATED : December 28, 1993

INVENTOR(S) : Jose C. Palathingal, et al.

It is certified that error appears in the above-identified patent and that said Letters Patent is hereby corrected as shown below:

Column 2, line 18, correct "1 keV//(mg/cm$^2$)" to read --1 keV/(mg/cm$^2$)--.

Column 2, line 41, correct "into" to read --not--.

Column 2, line 56, correct "and" to read --an--.

Column 7, line 4, insert --to the-- after "due".

Column 7, lines 52-53, correct "10$^6$ photons/-second" to read --10$^9$ photons/-second--.

Signed and Sealed this

Tenth Day of May, 1994

Attest:

BRUCE LEHMAN

Attesting Officer

Commissioner of Patents and Trademarks